United States Patent
Li et al.

(10) Patent No.: US 11,360,630 B1
(45) Date of Patent: Jun. 14, 2022

(54) TOUCH PANEL AND METHOD FOR FORMING TOUCH PANEL, TOUCH MODULE, AND TOUCH DISPLAY MODULE

(71) Applicant: Shanghai AVIC OPTO Electronics Co., Ltd., Shanghai (CN)

(72) Inventors: Liyan Li, Shanghai (CN); Lu Yao, Shanghai (CN); Feng Qin, Shanghai (CN)

(73) Assignee: Shanghai AVIC OPTO Electronics Co., Ltd., Shanghai (CN)

( * ) Notice: Subject to any disclaimer, the term of this patent is extended or adjusted under 35 U.S.C. 154(b) by 0 days.

(21) Appl. No.: 17/197,329

(22) Filed: Mar. 10, 2021

(30) Foreign Application Priority Data

Dec. 18, 2020 (CN) .......................... 202011505061.5

(51) Int. Cl.
  *G06F 3/044* (2006.01)
  *A61L 2/10* (2006.01)
  *G06F 3/041* (2006.01)

(52) U.S. Cl.
  CPC .............. *G06F 3/0446* (2019.05); *A61L 2/10* (2013.01); *G06F 3/0412* (2013.01)

(58) Field of Classification Search
  CPC ......... G06F 3/0446; G06F 3/0412; A61L 2/10
  See application file for complete search history.

(56) References Cited

U.S. PATENT DOCUMENTS

| | | | |
|---|---|---|---|
| 9,492,576 B1 | 11/2016 | Cudak | |
| 10,166,309 B2 * | 1/2019 | Liao | ........................ C02F 1/008 |
| 2015/0258228 A1 * | 9/2015 | Cohen | ................... G06F 3/0416 |
| | | | 250/492.1 |

FOREIGN PATENT DOCUMENTS

| | | |
|---|---|---|
| CN | 110310578 A | 10/2019 |
| KR | 101813077 B1 | 12/2017 |

* cited by examiner

*Primary Examiner* — Peter D McLoone
(74) *Attorney, Agent, or Firm* — Anova Law Group, PLLC (57) ABSTRACT

A touch panel and a method for forming a touch panel, a touch module and a touch display panel are provided. The touch panel includes a substrate including a touch area and a bonding area located at one side of the touch area; a plurality of touch electrodes located in the touch area; a plurality of touch leads connected with the plurality of touch electrodes in a one-to-one correspondence and extending to the bonding area; a plurality of ultraviolet light-emitting modules located in the touch area; and a plurality of light-emitting leads electrically connected with the plurality of ultraviolet light-emitting module in a one-to-one correspondence and extending to the bonding area.

20 Claims, 8 Drawing Sheets

TOUCH PANEL AND METHOD FOR FORMING TOUCH PANEL, TOUCH MODULE, AND TOUCH DISPLAY MODULE

CROSS-REFERENCE TO RELATED APPLICATION

This application claims the priority of Chinese Patent Application No. 202011505061.5, filed on Dec. 18, 2020, the content of which is incorporated by reference in its entirety.

TECHNICAL FIELD

The present disclosure generally relates to the field of display technology and, more particularly, relates to a touch panel and a method for forming a touch panel, a touch module, and a touch display module.

BACKGROUND

Medical self-service terminals, ATM machines of banks and other display panels are generally equipped with display screens for users to operate. The sweat and germs on the user's fingers will make the display screen very dirty and are difficult to erase. It is easy to breed microorganisms and bacteria, which affects users' health. The disclosed touch panels and methods for forming touch panels, touch modules and touch display modules are directed to solve one or more problems set forth above and other problems in the art.

SUMMARY

One aspect of the present disclosure provides a touch panel. The touch panel may include a substrate including a touch area and a bonding area located at one side of the touch area; a plurality of touch electrodes located in the touch area; a plurality of touch leads connected with the plurality of touch electrodes in a one-to-one correspondence and extending to the bonding area; a plurality of ultraviolet light-emitting modules located in the touch area; and a plurality of light-emitting leads electrically connected with the plurality of ultraviolet light-emitting module in a one-to-one correspondence and extending to the bonding area.

Another aspect of the present disclosure provides a touch module. The touch module may include a protection cover having a touch surface, a present disclosed touch panel disposed on a surface of the protection cover away from the touch surface. The plurality of ultraviolet light-emitting modules of the touch panel are disposed on the substrate facing the protection cover.

Another aspect of the present disclosure provides a touch display module. The touch display module may include a protection cover having a touch surface, a display panel disposed on a side of the protection cover away from the touch surface, a present disclosed touch panel disposed between and the display panel and the protection cover away. The plurality of ultraviolet light-emitting modules of the touch panel are disposed on the substrate facing the protection cover.

Another aspect of the present disclosure provides a method for forming a touch panel. The method may include providing a substrate; and forming a plurality of touch electrodes, a plurality of light-emitting electrodes, a plurality of touch leads and a plurality of light-emitting leads on the substrate. The plurality of touch leads may be electrically connected to the plurality of touch electrodes in a one-to-one correspondence and the plurality of light-emitting leads may be electrically connected to the plurality light-emitting electrodes in a one-to-one correspondence. The method may also include forming a plurality of ultraviolet light-emitting elements on each light-emitting electrode; and providing a voltage to the plurality of light-emitting electrodes to check if the plurality of ultraviolet light-emitting modules normally emit light.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

The features and exemplary embodiments of various aspects of the present disclosure will be described in detail below. In the following detailed description, many specific details are proposed to provide a comprehensive understanding of the present disclosure. However, it is obvious to those skilled in the art that the present disclosure can be implemented without some of these specific details. The following description of the embodiments is only to provide a better understanding of the present disclosure by showing examples of the present disclosure. In the drawings and the following description, at least a part of the well-known structures and technologies are not shown to avoid unnecessary blurring of the present disclosure; and, for clarity, the size of some structures may be exaggerated. In addition, the features, structures, or characteristics described below may be combined in one or more embodiments in any suitable manner. The orientation words appearing in the following description are all directions shown in the figure, and do not limit the specific structure of the present disclosure. In the description of the present disclosure, it should also be noted that, unless otherwise clearly specified and limited, the terms "installation" and "connection" should be understood in a broad sense, for example, it can be a fixed connection or a detachable connection, or integrally connected. It can be directly connected or indirectly connected. For those of ordinary skill in the art, the specific meaning of the above-mentioned terms in the present disclosure can be understood according to specific circumstances.

Figure 1:
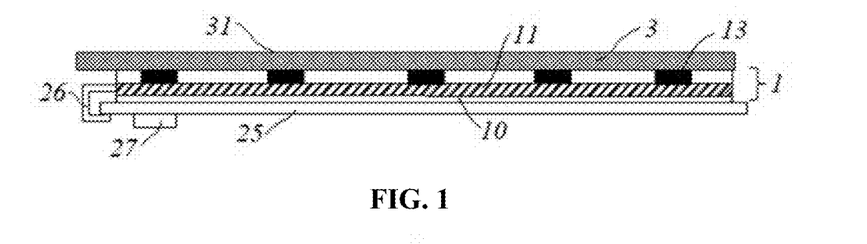
FIG. 1 illustrates an exemplary touch module consistent with various disclosed embodiments of the present disclosure.
Figure 2:
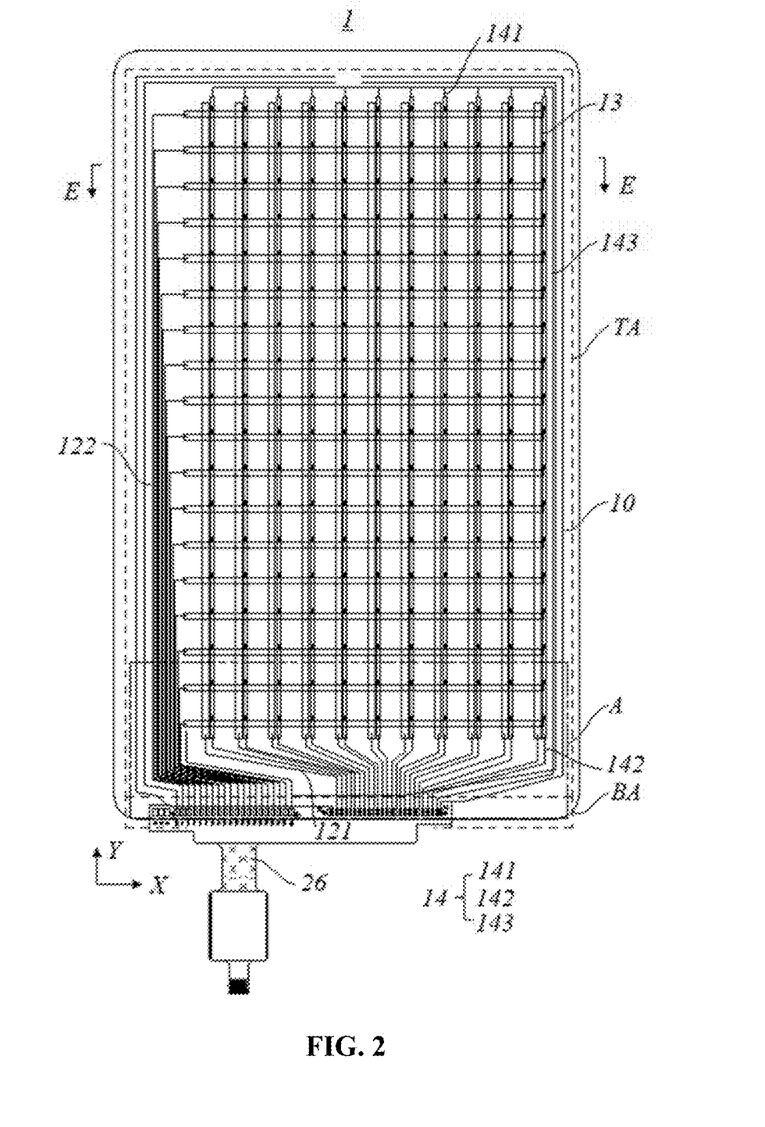
FIG. 2 illustrates an exemplary touch panel of the touch module in FIG. 1.
Figure 3:
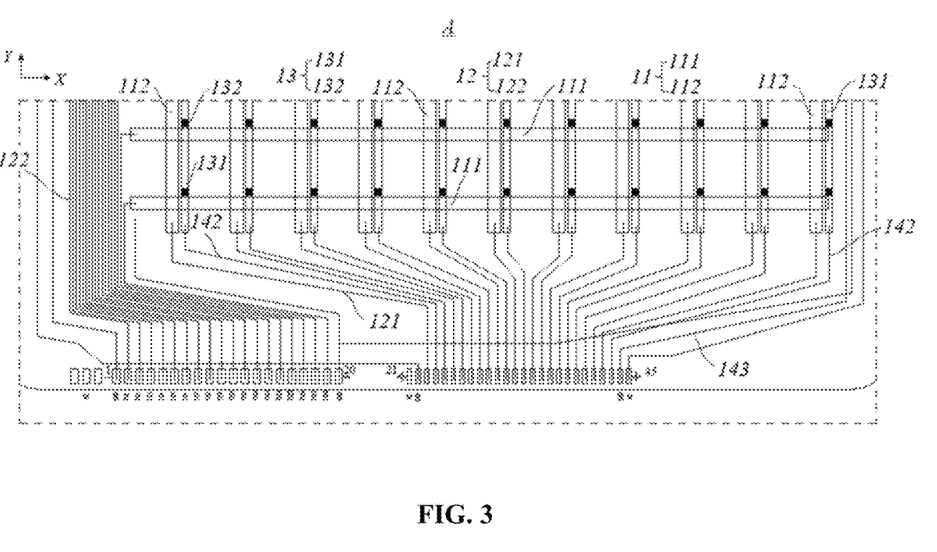
FIG. 3 is a zoomed-in view of the region A of the touch panel in FIG. 2.

The present disclosure provides a touch module. The touch module may be a portable notebook or a handwriting tablet with the touch function. As a human-computer interactive input method, the touch module may be simpler, more direct, and convenient than the keyboard and mouse input methods of traditional displays. FIG. 1 illustrates a schematic structural diagram of an exemplary touch module consistent with various disclosed embodiments of the present disclosure. FIG. 2 illustrates a schematic structural diagram of an exemplary touch panel of the touch module shown in FIG. 1. FIG. 3 illustrates a zoomed-in view of the area A of the touch panel in FIG. 3.

As shown in FIGS. 1-3, the touch module may include a touch panel 1 and a protection cover 3. The protection cover 3 may have a touch surface 31 for protecting the touch panel 1 from external dust and moisture. The touch panel 1 may be disposed on the side of the protection cover 3 away from the touch surface 31, and the touch panel 1 may configured to sense touch events, such as an actual touch with the touch panel 1 or a nearby touch interacting with the touch panel 1. The user may operate the touch module by touching the protection cover 3. Because the sweat, germs, etc. on the user's fingers will touch the protection cover 3, and the sweat and the germs may not be easy to erase, it is easy to breed microorganisms and bacteria, which may affect the health of the user.

Thus, the present disclosure provides a touch panel 11. The touch panel 11 may include a substrate 10, a plurality of touch electrodes 11, a plurality of touch leads 12, a plurality of ultraviolet light-emitting modules 13 and a plurality of light-emitting leads 14. The substrate 10 may include a touch area TA and a bonding area BA located on one side of the touch area TA. The plurality of touch electrodes 11 may be disposed in the touch area TA, and the plurality of touch leads 12 may be connected to the plurality of touch electrodes 11 in a one-to-one correspondence and may extend to the bonding area BA. The plurality of ultraviolet light-emitting modules 13 may be disposed in the touch area TA, and the plurality of light-emitting leads 14 may be connected to the plurality of ultraviolet light-emitting modules in a one-to-one correspondence, and may extend to the bonding area BA. The ultraviolet light-emitting modules 13 may emit ultraviolet (UV) light, which is the invisible light out of the visible light (red, orange, yellow, green, blue, and purple) of the sunlight, and the UV light is a general term for the radiation have a wavelength from 10 nm to 400 nm in the electromagnetic spectrum.

According to the different wavelengths, ultraviolet rays are generally divided into three bands: A, B, and C, as follows: the wavelength of UVA is 400-315 nm, the wavelength of UVB is 315-280 nm, and the wavelength of UVC is 280-100 nm. Among them, due to its short wavelength and high energy, UVC may be able to destroy the molecular structure of DNA (deoxyribonucleic acid) or RNA (ribonucleic acid) in microbial organisms (bacteria, viruses, spores, and other pathogens) in a short time, the cells are unable to regenerate, and bacteria and viruses lose the ability to replicate themselves. Thus, the UVC band products may be widely used for sterilization and disinfection of water and air.

In one embodiment, the ultraviolet light-emitting module 13 may be ultraviolet light-emitting diodes (UV-LEDs), which may be used as a light source for UV sterilization due to its small size. To reduce the thickness of the touch module, the UV-LEDs may be micro-light emitting diodes (Micro-LEDs) that emit ultraviolet light. The micro-light emitting diode may a grain size of 100 microns or less, with the advantages of low power consumption, high brightness, high resolution, high color saturation, fast response speed, longer life span, and higher efficiency, etc.

To sterilize the touch surface 31 of the protection cover 3, the ultraviolet light-emitting modules 13 may be disposed on the side of the substrate 10 of the touch panel 1 facing the protection cover 3. Further, the protection cover 3 may be made of a ultraviolet transmittable material. In one embodiment, the material of the protection cover 3 is a material including quartz.

As shown in FIG. 2, the plurality of touch electrodes 11 may be disposed in rows and columns in the touch area TA of the substrate 10, and the plurality of ultraviolet light-emitting modules 13 may also be integrated in the touch area TA such that the touch leads 12 electrically connected with each touch electrode 11 and the light-emitting leads 14 electrically connected to each ultraviolet light-emitting module 13 may together extend to the bonding area BA.

Further, as shown in FIG. 1, the touch module may also include a flexible circuit board 26, a main circuit board 25, and a control chip 27 disposed on the main circuit board 25. One end of the flexible circuit board 26 may be connected to the bonding area BA of the touch panel 1, and the other end may be bonded and connected to the main circuit board 25 to electrically connect plurality of touch electrodes 11 and the plurality of ultraviolet light-emitting modules 13 with the main circuit board 25 to allow the main circuit board 25 to supply power to the touch electrodes 11 and the ultraviolet light-emitting modules 13. Further, the control chip 27 on the main circuit board 25 may control to turn on and off the ultraviolet light-emitting modules 13.

In the present disclosure, the touch module may include two modes: working mode and sterilization mode. In the working mode, the plurality of ultraviolet light-emitting modules 13 may be turned off, and the touch module may be configured to sense touch events. In the sterilization and disinfection mode, the plurality of ultraviolet light-emitting modules 13 may be turned on to sterilize the protection cover 3.

In some embodiments, the driving chip 27 of the main circuit board 25 may further includes a delay unit. The delay unit may be configured to receive first information for turning on the sterilization and disinfection mode, and according to the first information, to send second information for turning on the plurality of ultraviolet light-emitting modules 13 to the plurality of ultraviolet light-emitting modules 13 after a pre-determined delay time length. When the touch display module is in the sterilization and disinfection mode, the ultraviolet light-emitting modules 13 may be lighted on after a pre-determined delay time length after the UV light emitting units 13 are turned on to reserve time for the user to leave the touch module and prevent the ultraviolet light from harming the human body. After the sterilization is completed, the protection cover 3 may be in a relatively clean state, the touch module may automatically switch to the working mode, and the user can operate the touch module normally.

The present disclosure provides a touch panel 1 and a touch module. The substrate 10 of the touch panel 1 may include a touch area TA and a bonding area BA located at one side of the touch area TA. The plurality of touch electrodes 11 and the plurality of ultraviolet light-emitting modules 13 may be disposed in the touch area TA, and the touch lead 12 electrically connected to each touch electrode 11 and the light-emitting lead 14 electrically connected to each ultraviolet light-emitting module 13 may extend to the bonding area BA to automatically sterilize the touch surface of the touch module. Thus, the cross-infection of users may be avoided, and the user experience may be improved.

Figure 4:
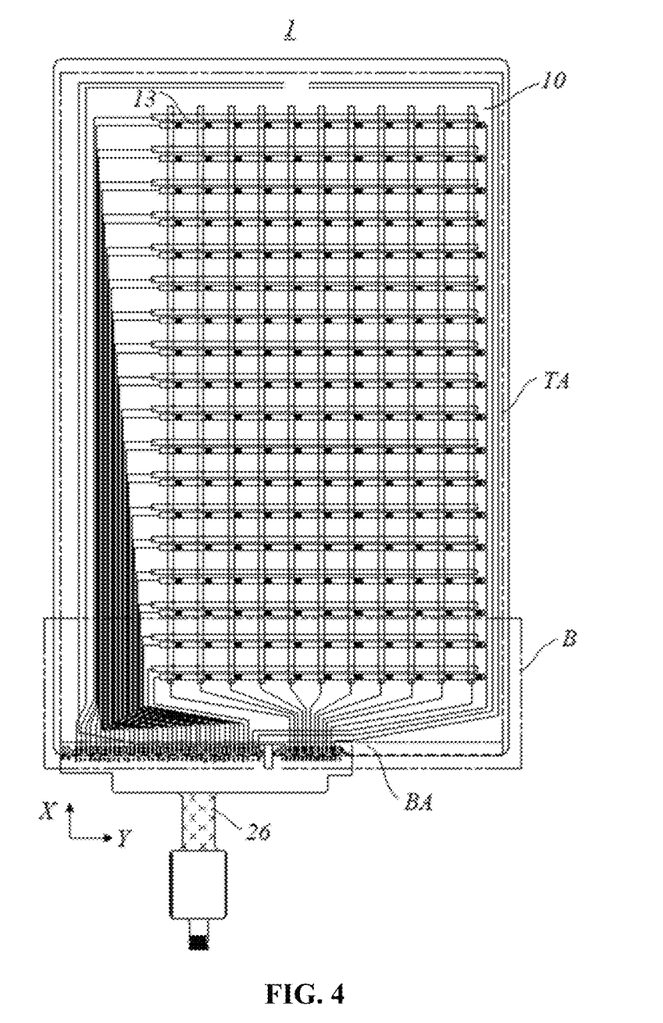
FIG. 4 illustrates another exemplary touch panel of the touch module in FIG. 1.
Figure 5:
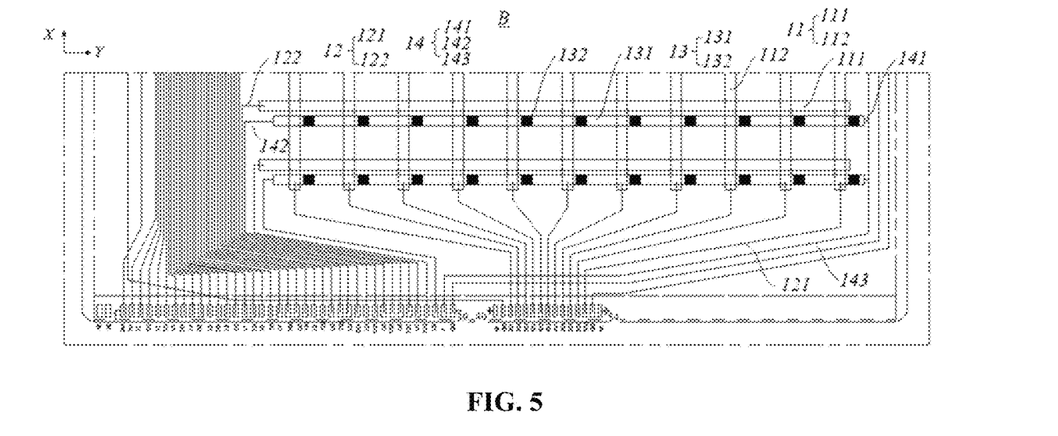
FIG. 5 is a zoomed-in view of the region B of the touch panel in FIG. 2.

FIG. 4 illustrates a schematic structural diagram of another exemplary touch panel of the touch display module in FIG. 1. FIG. 5 illustrates a zoomed-in view of the area B of the touch panel in FIG. 4.

As shown in FIGS. 2-5, the plurality of ultraviolet light-emitting modules 13 may be arranged in parallel along a first direction X. Each ultraviolet light-emitting module 13 may include a light-emitting electrode 131 extending along a second direction Y and a plurality of ultraviolet light-emitting elements 132 electrically connected to the light-emitting electrode 131. The plurality of ultraviolet light-emitting elements 132 may be bonded to the light-emitting electrode 131 by a surface mount technology (SMT), or a chip on board (COB) technology. The plurality of ultraviolet light-emitting elements 132 may be distributed spaced apart along the second direction Y. The first direction X may intersect the second direction Y. In one embodiment, the first direction X may be perpendicular to the second direction Y to simplify the processing technology of the touch panel 1. Thus, the plurality of ultraviolet light-emitting elements 132 of the plurality of ultraviolet light-emitting modules 13 may be arranged in an array in the plane where the first direction X and the second direction Y are located and may jointly emit the UV light toward the protection cover 3 to sterilize and disinfect the protection cover 3.

Further, the plurality of touch electrodes 11 may include a plurality of first electrodes 111 and a plurality of second electrodes 112 that are insulated from each other, and any one of each first electrode 111 and each second electrode 112 may be disposed along the second direction Y and in parallel with each light-emitting electrode 131, and the other of the each first electrode 111 and the each second electrode 112 may extend along the first direction X. The first electrode 111, the second electrode 112, and the light-emitting electrode 131 may be made of a transparent conductive material, such as aluminum zinc oxide (AZO), gallium zinc oxide (GZO), or indium zinc oxide (ITO), etc.

The working principle of the touch panel 1 may be as follow. When a finger approaches or touches the plane where the plurality of touch electrodes 11 are located, the finger may be equivalent to a conductor, and the capacitance of the finger will be superimposed on the capacitance of the touch panel 1, and the capacitance of the touch panel 1 may be increased. During the touch detection, the touch panel 1 may detect the plurality of first electrodes 111 and the plurality of second electrodes 112 in sequence, and may determine the coordinates along the first direction X and the coordinates along the second direction Y according to the changes in capacitance before and after the touch; and then combined into a flat touch coordinate. The procedure may be equivalent to projecting the touch points on the touch panel 1 to the X-axis and Y-axis directions, and then calculate the coordinates in the X-axis and Y-axis directions, and finally combine them into the coordinates of the touch points.

The plurality of touch electrodes 11 of the touch panel 1 may be capacitive touch electrodes, including two methods: self-capacitance and mutual capacitance. In one embodiment, the plurality of touch electrodes 11 of the touch panel 1 are self-capacitive. For example, each touch electrode 11 forms a capacitor with the ground. Each touch electrode 11 may be connected to the control chip through its own touch lead 12, and the touch lead 12 may be configured to send a touch driving signal sent from the control chip to each touch electrode 11, and the touch electrode 11 may send the touch sensing signal generated by the touch electrode 11 back to the control chip 27 through the same touch lead 12. The plurality of touch electrodes 11 may receive the pulse information signals sent by the control chip 27 to form a phase shift network on the entire plane.

In one embodiment, the plurality of touch electrodes 11 of the touch panel 1 are of mutual capacitance type. For example, the position where the first electrode 111 and the second electrode 112 intersect may form a capacitor. Any one of the first electrode 111 and the plurality of second electrodes 112 may be a touch driving electrode, and the other one of the first electrode 111 and the plurality of second electrodes 112 may be a touch sensing electrode. When an excitation signal is applied to the touch driving electrode, due to the existence of mutual capacitance, the excitation signal can be sensed and received on the touch sensing electrode. The value and the phase shift of the received signal, and the frequency of the excitation signal may be related to the value of the mutual capacitor. For example, the touch position may be determined according to the capacitance between the touch driving electrode and the touch sensing electrode.

In some embodiments, as shown in FIGS. 2-3, the light-emitting electrode 131 of each ultraviolet light-emitting module 13 may extend along the second direction Y, and may be disposed in parallel with each second electrode 112. Each first electrode 111 may extend along the first direction X. The first electrode 111 and the second electrode 112 may identify the touch of a part of the body, such as a finger and hand of the human body or a stylus pen, etc. For example, the first electrode 111 may be able to recognize the coordinates of the touch position along the first direction X, and the second electrode 112 may be able to recognize the coordinates of the touch position along the second direction Y. The coordinates of each touched position may be identified by the first electrode 111 and the second electrode 112 to response the touch operation of the user and display the corresponding image.

In some embodiments, as shown in FIGS. 4 and 5, the plurality of ultraviolet light-emitting modules 13 may be disposed in parallel along the first direction X, and the light-emitting electrode 131 of each ultraviolet light-emitting module 13 may extend along the second direction Y and may be disposed in parallel with each first electrode. Each second electrode 112 may extend along the first direction X. The first electrode 111 and the second electrode 112 may identify a part of the body such as a finger and a hand of the human body or the touch of a stylus. For example, the first electrode 111 may be able to recognize the coordinates of the touch position along the second direction Y, and the second electrode 112 may be able to recognize the coordinates of the touch position along the first direction X. The coordinates of each touched position may be identified by the first electrode 111 and the second electrode 112 to response the user's touch operation to display the corresponding image.

For ease of description, the touch panel shown in FIG. 2 and FIG. 3 is taken as an example for description.

Figure 6:
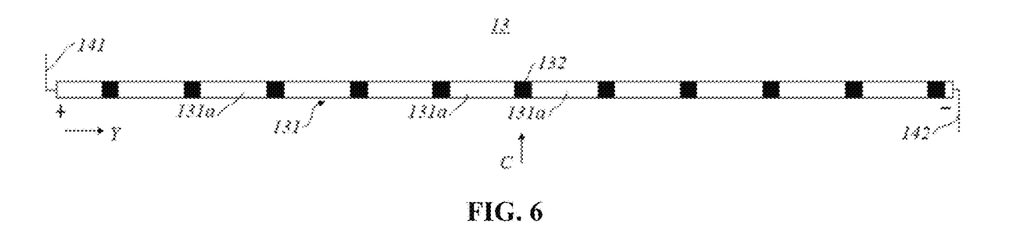
FIG. 6 illustrates an exemplary ultraviolet light-emitting module of the touch panel in FIG. 2.
Figure 7:
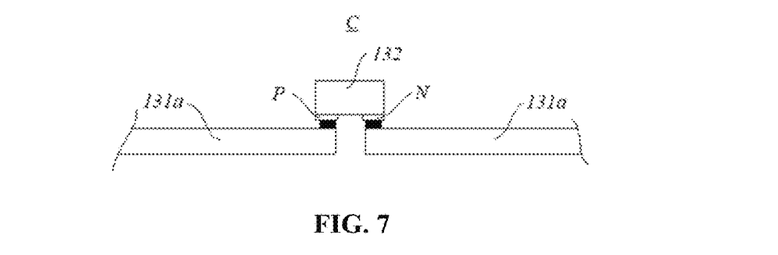
FIG. 7 illustrates a partial view of the ultraviolet light-emitting module in FIG. 6 along the direction C.

FIG. 6 illustrates a schematic structural diagram of an ultraviolet light-emitting module of the touch panel shown in FIG. 2. FIG. 7 illustrates a partial structural diagram of the ultraviolet light-emitting module shown in FIG. 6 as viewed along the direction C.

Referring to FIG. 2, FIG. 3, FIG. 6, and FIG. 7, in some embodiments, the ultraviolet light-emitting element 132 may has a first terminal P and a second terminal N, and the light-emitting electrode 131 may include a plurality of sub light-emitting electrodes 131a spaced apart along the second direction Y. Each sub light-emitting electrode 131a may include a first and a second end opposing to each other. In every two adjacent sub light-emitting electrodes 131a, the second end of one of the sub light-emitting electrodes 131a may be electrically connected to the first terminal P of the ultraviolet light-emitting element 132; and the first end of anther the sub light-emitting electrode 131a may be electrically connected to the second terminal N of the ultraviolet light-emitting element 132.

In one embodiment, the first terminal P of the ultraviolet light-emitting element 132 may be a positive electrode, and the second terminal N may be a negative electrode. The first end and the second end of each sub light-emitting electrode 131a may be respectively provided with a pad. The first terminal P of each ultraviolet light-emitting element 132 may be electrically connected to the pad of the second end of one of the sub light-emitting electrodes 131a, and the second terminal N of each the ultraviolet light-emitting element 132 may be electrically connected to the pad of the first terminal of the other sub light-emitting electrode 131a. Thus, the plurality of ultraviolet light-emitting elements 132 of each ultraviolet light-emitting module 13 may be connected in series along the second direction Y. Among the plurality of light-emitting sub-electrodes 131a, one light-emitting sub-electrode 131a located on one side of the second direction Y may the positive terminal, one light-emitting sub-electrode 131a located on the other side of the second direction Y may be the negative terminal. The light-emitting lead 14 may be electrically connected to the positive terminal and the negative terminal, and may extend to the bonding area BA.

In some embodiments, the plurality of light-emitting leads 14 may include a plurality of first light-emitting leads 141, a plurality of second light-emitting leads 142, and a third light-emitting lead 143. The light-emitting leads 14 may be made of a metal conductive material.

Each first light-emitting lead 141 may be electrically connected to the light-emitting sub-electrode 131a of the multiple sub light-emitting electrodes 131a of each ultraviolet light-emitting module 13 at one end along the second direction Y. Each second light-emitting lead 142 may be electrically connected to the light-emitting sub-electrode 131a of the plurality of light-emitting sub-electrodes 131a of each ultraviolet light-emitting module 13 at another end along the second direction. The third light-emitting lead 143 may be electrically connected to the plurality of first light-emitting leads 141. The third light-emitting lead 143 and the plurality of second light-emitting leads 142 may respectively extend to the bonding area BA, as shown in FIG. 2.

Further, the plurality of touch leads 12 may include a plurality of first touch leads 121 electrically connected to one end of each first electrode 111 and two first ground leads, and a plurality of second touch leads 122 electrically connected to one end of each second electrode 112 and two second ground leads. The plurality of first touch leads 121, the two first ground leads, the plurality of second touch leads 122 and the two second ground leads may respectively extend to the bonding area BA. The plurality of touch leads 12 may be made of a metal conductive material.

As shown in FIGS. 2-3, the plurality of first light-emitting leads 141 may correspond to the positive terminals of the plurality of ultraviolet light-emitting modules 13, and the third light-emitting lead 143 may be electrically connected to the plurality of first light-emitting leads 141, which is equivalent to the common positive terminal of the plurality of ultraviolet light-emitting modules 13. The plurality of second light-emitting leads 142 may correspond to the negative terminals of the plurality of ultraviolet light-emitting modules 13. There may be forty five pad leads in the bonding area BA. The pad leads 1-20 may correspond to the plurality of touch electrodes 11 extending along the first direction X, and the pad leads 21-45 may correspond to the plurality of touch electrodes 11 and the plurality of sub light-emitting electrodes 131 extending along the second direction Y.

For example, among the plurality of pad leads 1-20 in the bonding area BA, the pad leads 2-19 may be respectively electrically connected to the plurality of second touch leads 122, and the pad leads 1 and 20 may be electrically connected to the ground leads to electrically connect the plurality of second electrodes 112 with the bonding area BA, respectively. Among the plurality of pad leads 21-45 in the bonding area BA, the odd number pad leads 23, 25, 27 . . . and 43 may be electrically connected to the plurality of second light-emitting leads 142. The pad lead 44 may be electrically connected to the third light-emitting lead 143 to electrically connect the anode and the cathode of the plurality of ultraviolet light-emitting elements 132 to the bonding area BA. The even number pad leads, such as 22, 24, 26 . . . and 42, may be respectively connected to the plurality of first touch leads 121. The pad leads 21 and 45 may be electrically connected to the ground leads to electrically connect the plurality of first electrodes 111 to the bonding area BA, respectively.

Figure 8:
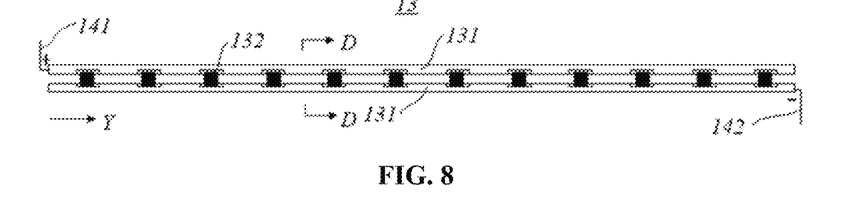
FIG. 8 illustrates another exemplary ultraviolet light-emitting module of the touch panel in FIG. 2.
Figure 9:
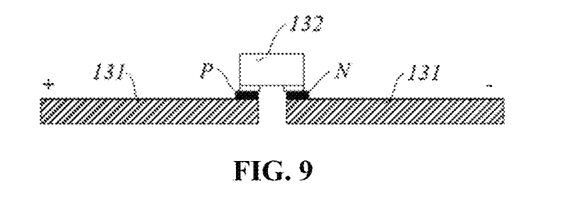
FIG. 9 illustrates a D-D-sectional view of the ultraviolet light-emitting module in FIG. 8.

FIG. 8 illustrates a schematic structural diagram of another ultraviolet light-emitting module in the touch panel shown in FIG. 2. FIG. 9 illustrates a schematic D-D-sectional view of the ultraviolet light-emitting module in FIG. 8.

As shown in FIGS. 8-9, in some embodiments, the ultraviolet light-emitting module 13 may include two light-emitting electrodes 131 arranged side by side. The ultraviolet light-emitting element 132 may include a first terminal P and a second terminal N. The first terminal P of the ultraviolet light-emitting element 132 may be electrically connected to one of the light-emitting electrodes 131, and the second terminal N of the ultraviolet light-emitting element 132 may be electrically connected to the other light-emitting electrode 131. As shown in FIG. 9, the first terminal P and the second terminal N of the ultraviolet light-emitting element 132 may be disposed below the light-emitting body. Further, the first terminal P and the second terminal N of the ultraviolet light-emitting element 132 may also be disposed on both sides of the light-emitting body.

Taking the first terminal P and the second terminal N of the ultraviolet light-emitting element 132 shown in FIG. 9 as an example, the two light-emitting electrodes 131 may be a positive electrode and a negative electrode, respectively. A plurality of pads may be disposed and spaced between the light-emitting electrodes 131 along the second direction Y. The first terminal P of the ultraviolet light-emitting element 132 may be electrically connected to the pad of the positive electrode of one of the light-emitting electrodes 131, and the second terminal N of the ultraviolet light emitting element 132 may be electrically connected to the pad of the negative electrode of the other light-emitting electrode 131.

Further, the plurality of light-emitting leads 14 may include a plurality of first light-emitting leads 141, a plurality of second light emitting-leads 142, and a third light-emitting lead 143. The light-emitting leads 14 may be made of a metal conductive material.

Referring to FIG. 2 and FIG. 8, in the two light-emitting electrodes 131, one light-emitting electrode 131 may be a positive electrode, and the other light-emitting electrode 131 may be a negative electrode. Each first light-emitting lead 141 may be electrically connected to one light-emitting electrode 131 (for example, the positive anode) of each ultraviolet light-emitting module 13, and each second light-emitting lead 142 may be electrically connected to another light-emitting electrode 131 (for example, the negative electrode) of each ultraviolet light-emitting module 13. The third light-emitting lead 143 may be electrically connected to a plurality of first light-emitting leads 141 to form a common positive lead. The third light-emitting lead 143 as the common positive lead and the plurality of second light-emitting leads 142 as the negative leads may respectively extend to the bonding area BA.

Thus, the plurality of ultraviolet light-emitting elements 132 of each ultraviolet light-emitting module 13 may be connected in parallel with each other along the second direction Y. If one of the ultraviolet light-emitting elements 132 fails, it may not affect the other ultraviolet light-emitting element 132 of the ultraviolet light unit 13 to continue the sterilization.

It can be understood that the structure of the ultraviolet light-emitting module 13 shown in FIGS. 6-9 may also be applicable to the touch panel 1 described in FIGS. 4-5, and the detail will not be repeated.

Figure 10:
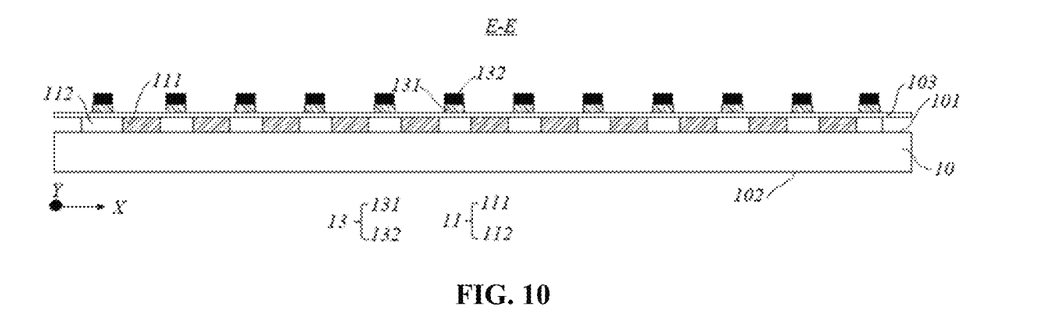
FIG. 10 illustrates an E-E-sectional view of the touch panel in FIG. 2.

FIG. 10 illustrates another E-E-sectional view of the touch panel shown in FIG. 2. As shown in FIG. 10, in some embodiments, the substrate 10 may include a first surface 101 and a second surface 102 opposite to each other, a plurality of touch electrodes 11 disposed on the first surface 101, and a plurality of ultraviolet light-emitting modules 13 disposed on a side of the plurality of touch electrodes 11 facing away from the substrate 10. The first surface 101 may be located on the side of the substrate 10 facing the protection cover 3. The substrate 10 may be a rigid substrate, such as glass, or a flexible substrate, such as polyethylene terephthalate (PET), etc.

In such an embodiment, the touch electrode 11 of the touch panel 1 may be a single-layer structure. Generally, the self-capacitance screen is a single-layer structure, and the mutual-capacitance screen may also be a single-layer structure. For example, the first electrode 111 and the second electrode 112 may be located on the same layer of the substrate 10, for example, both are located on the first surface 101. Such a configuration may facilitate the preparation of the touch electrode 11. The first electrode 111 may extend along the second direction Y, and the second electrode 112 may extends along the first direction X. The ultraviolet light-emitting module 13 may be arranged in parallel with either the first electrode 111 or the second electrode 112. For example, the ultraviolet light-emitting module 13 may be arranged in parallel with the first electrode 111.

Further, the first electrode 111 and the second electrode 112 may be insulated from each other. Thus, the first surface 101 of the substrate 10 may also be provided with a first insulating layer between the first electrode 111 and the second electrode 112 (not shown in the figure). A second insulating layer 103 may further be provided between the plurality of ultraviolet light-emitting modules 13 and the plurality of touch electrodes 11.

Figure 11:
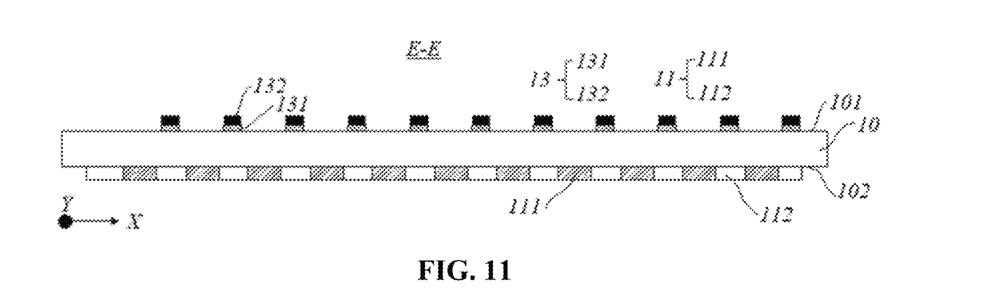
FIG. 11 illustrates an E-E-sectional view of an alternative touch panel consistent with various disclosed embodiments of the present disclosure.

FIG. 11 shows a schematic diagram of an E-E-sectional view of an alternative touch panel consistent with various disclosed embodiments of the present disclosure. As shown in FIG. 11, in some embodiments, the substrate 10 may include a first surface 101 and a second surface 102 opposing to each other, a plurality of ultraviolet light-emitting modules 13 disposed on the first surface 101, and a plurality of first electrodes 11 and a plurality of second electrodes 11 disposed on the second surface 102. The substrate 10 may be a rigid substrate, such as glass, or a flexible substrate, such as polyethylene terephthalate (PET or PETP), etc.

In such an embodiment, the touch electrode 11 of the touch panel 1 may be a single-layer structure. Generally, the self-capacitance screen may be a single-layer structure, and the mutual-capacitance screen may also be a single-layer structure. For example, the first electrode 111 and the second electrode 112 may be located on the same layer of the substrate 10, such as the second surface 102. The plurality of ultraviolet light-emitting modules 13 may be located on another layer of the substrate 10, such as the first surface 101. The first surface 101 may be located on the side of the substrate 10 facing the protection cover 3. The first electrode 111 may extend along the second direction Y, and the second electrode 112 may extend along the first direction X. The ultraviolet light-emitting modules 13 may be arranged in parallel with either the first electrode 111 or the second electrode 112, for example, the ultraviolet light-emitting module 13 may be arranged in parallel with the first electrode 111. Because the first electrode 111 and the second electrode 112 may be insulated from each other, an insulating layer (not shown in the figure) between the first electrode 111 and the second electrode 112 may also be provided on the second surface 102 of the substrate 10.

Figure 12:
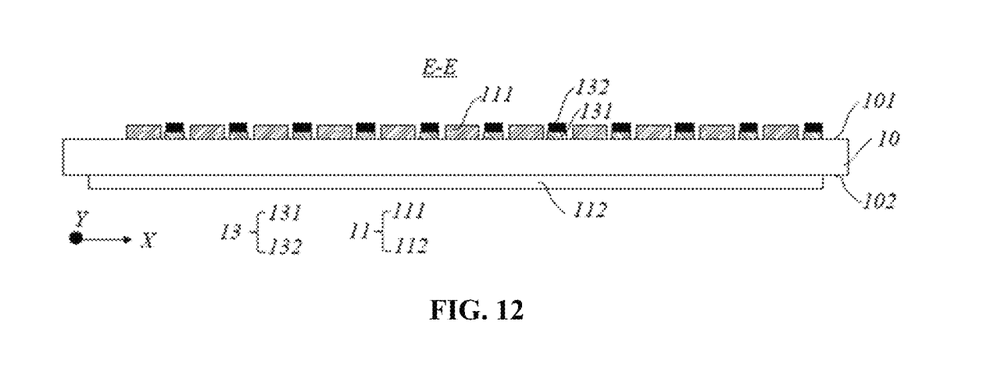
FIG. 12 illustrates another E-E-sectional view of an alternative touch panel consistent with various disclosed embodiments of the present disclosure.

FIG. 12 illustrates an exemplary E-E cross-sectional view of another alternative touch panel consistent with various disclosed embodiments of the present disclosure. As shown in FIG. 12, in some embodiments, the substrate 10 may include a first surface 101 and a second surface 102 opposing to each other, a plurality of ultraviolet light-emitting modules 13, and a plurality of first electrodes 111 and a plurality of second electrodes 112. One of the plurality of first electrodes 111 and the plurality of second electrodes 112 may be disposed on the first surface 101, and the other of the plurality of first electrodes 111 and the plurality of second electrodes 112 may be located on the second surface 102. The substrate 10 may be a rigid substrate, such as glass, or a flexible substrate, such as polyethylene terephthalate (PET or PETP), etc.

In such an embodiment, the touch electrode 11 of the touch panel 1 may be a double-layer structure. Generally, the mutual capacitance screen body may be a double-layer structure. For example, the first electrode 111 and the second electrode 112 may be disposed on different layers of the substrate 10, and the plurality of ultraviolet light emitting units 13 may be disposed in parallel with either the first electrode 111 or the second electrode 112. For example, the plurality of ultraviolet light-emitting modules 13 and the plurality of first electrodes 111 may be disposed on the first surface 101 in parallel, and the plurality of second electrodes 112 may be disposed on the second surface 102. The first surface 101 may be located on the side of the substrate 10 facing the protection cover 3. Each first electrode 111 may extend along the second direction Y, and each second electrode 112 may extend along the first direction X. Each ultraviolet light-emitting module 13 may be parallel to either the first electrode 111 or the second electrode 112. For example, each ultraviolet light-emitting module 13 may be disposed in parallel with the first electrode 111.

Further, when the touch electrode 11 of the touch panel 1 is a double-layer structure, the flexible circuit board 26 that is bonded and connected to the bonding area BA of the substrate 10 may be Y-shaped. For example, the flexible circuit board 26 may include three parts. The first part may be electrically connected to the main circuit board 25, the second part and the third part are bifurcated by the first part. The second part may be electrically connected to the plurality of first electrodes 111 and the plurality of ultraviolet light-emitting modules 13 of the bonding area BA corresponding to the first surface 101. The third part may be electrically connected to the plurality of second electrodes 112 of the bonding area BA corresponding to the second surface 102.

Figure 13:
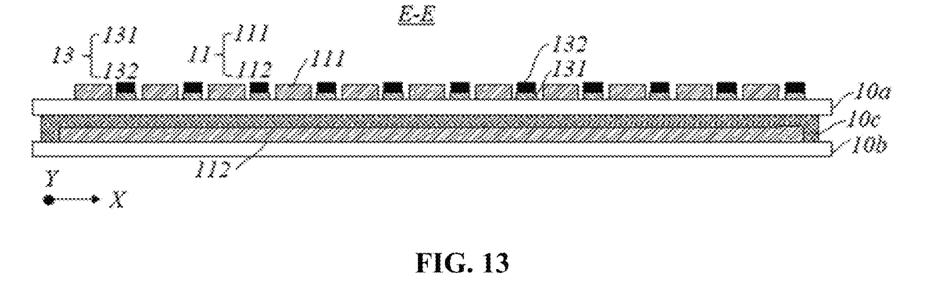
FIG. 13 illustrates another E-E-sectional view of an alternative touch panel consistent with various disclosed embodiments of the present disclosure.

FIG. 13 illustrates an exemplary E-E-sectional view of another alternative touch panel consistent with various disclosed embodiments of the present disclosure. As shown in FIG. 13, in some embodiments, the substrate 10 may include a first flexible substrate 10a and a second flexible substrate 10b that are insulated from each other, a plurality of ultraviolet light-emitting modules 13, a plurality of first electrodes 111 and a plurality of second electrodes 112. The plurality of ultraviolet light-emitting modules 12 and any one of the plurality of first electrodes 11 and the plurality of second electrodes 112 may be located on the first flexible substrate 10a, and the other of the plurality of first electrodes 111 and the plurality of second electrodes 112 may be located on the side of the second flexible substrate 10b facing the first flexible substrate 10a. In one embodiment, the first flexible substrate 10a may be disposed facing the protection cover 3. The first flexible substrate 10a and the second flexible substrate 10b may be made of transparent polyethylene terephthalate (PET or PETP), etc.

In such an embodiment, the touch electrode 11 of the touch panel 1 may be a double-layer structure. Generally, the mutual capacitance screen body may be a double-layer structure. To make the plurality of first electrodes 111 and the plurality of second electrodes 112 insulated from each other, the first flexible substrate 10a and the second flexible substrate 10b may be insulated from each other. For example, the first flexible substrate 10a and the second flexible substrate 10b may be insulated from each other. An insulating layer 10c may also be disposed between the first flexible substrate 10a and the second flexible substrate 10b. The plurality of ultraviolet light-emitting modules 13 and the plurality of first electrodes 111 may be disposed on the first flexible substrate 10a, and the plurality of second electrodes 112 may be disposed on the second flexible substrate 10b. Each first electrode 111 may extend along the second direction Y, and each second electrode 112 may extend along the first direction X. Each ultraviolet light-emitting module 13 may be arranged in parallel with the first electrode 111.

Figure 14:
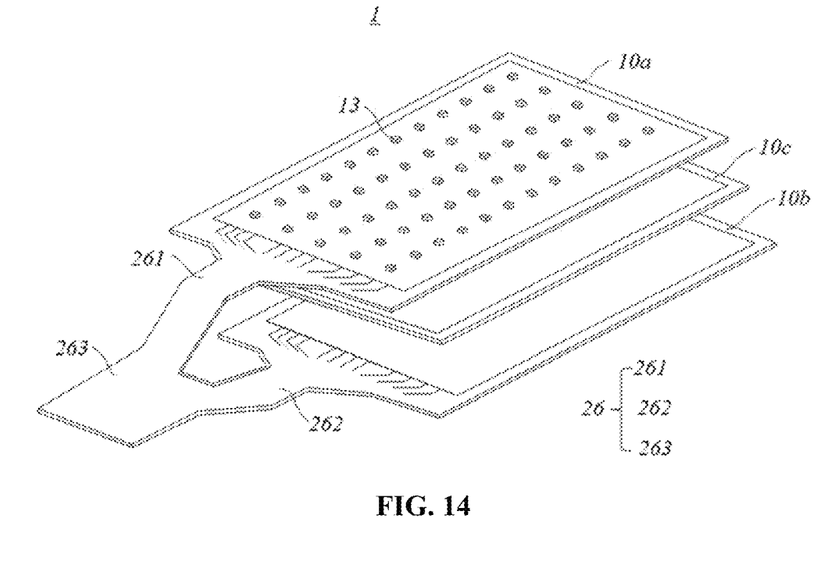
FIG. 14 illustrates an exemplary assembly of the touch panel and the flexible circuit board in FIG. 13.

FIG. 14 illustrates an exemplary assembly structure of the touch panel and the flexible circuit board shown in FIG. 13. As shown in FIG. 14, the touch electrode 11 of the touch panel 1 may be a double-layer structure. The substrate 10 may include a first flexible substrate 10a, a second flexible substrate 10b, and an insulating layer 10c between the first flexible substrate 10a and the second flexible substrate 10b. A plurality of first electrodes 111 (not shown in the figure) and a plurality of ultraviolet light-emitting modules 13 may be disposed on the first flexible substrate 10a, and a plurality of second electrodes 112 (not shown in the figure) may be disposed on the second flexible substrate 10b. Referring to FIG. 1, one end of the flexible circuit board 26 may be bonded and connected to the bonding area BA of the substrate 10, and the other end may be electrically connected to the main circuit board 25. The flexible circuit board 26 may be Y-shaped. For example, the flexible circuit board 26 may include a first part 261, a second part 262 and a third part 263. The third part 263 may be electrically connected to the main circuit board 25. The first part 261 and the second part 262 may be bifurcated by the third part 263. The first part 261 may be electrically connected to the plurality of first electrodes 111 in the bonding area BA corresponding to the first flexible substrate 10a and the plurality of ultraviolet light-emitting modules 13. The second part 262 may be electrically connected to the plurality of second electrodes 112 in the bonding area BA corresponding to the second flexible substrate 10b.

It can be understood that the above-mentioned laminated structure of the touch panel 1 shown in FIGS. 10-13 may also be applicable to the touch panel 1 described in FIGS. 4-5, and the details is not repeated.

Figure 15:
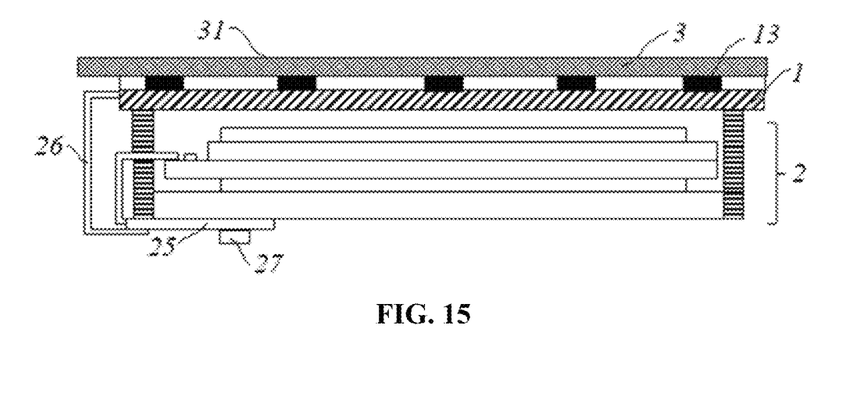
FIG. 15 illustrates an exemplary touch display module consistent with various disclosed embodiments of the present disclosure.

The present disclosure also provides a touch display module. FIG. 15 illustrates an exemplary touch display module consistent with various disclosed embodiments of the present disclosure.

As shown in FIG. 15, the touch display module may include a touch panel 1, a display panel 2 and a protection cover 3. The touch panel may be a present disclosed touch panel described previously, or other appropriate touch panel.

The protection cover 3 may have a touch surface 31 for protecting the touch panel 1 from external dust and moisture.

The display panel 2 may be disposed on the side of the protection cover 3 away from the touch surface 31. The display panel 2 may be any one of an organic light-emitting diode (OLED) display panel, a light-emitting diode (LED) display panel, or a liquid crystal display (LCD) panel.

The touch panel 1 may be disposed between the display panel 2 and the protection cover 3. The plurality of ultraviolet light-emitting modules 13 of the touch panel 1 may be disposed on the side of the substrate 10 facing the protection cover 3.

The touch display module may be applied to medical self-service terminals, or bank auto transition machines (ATMs), etc. The user may operate the touch display module by touching the touch surface 31 of the protection cover 3, for example, to query personal information, print reports, and so on. Because the sweat, and/or germs, etc. on the user's fingers touch the protective cover 3, and they are not easy to erase, it may be easy to breed microorganisms and bacteria, which may affect the health of the user. The UV light emitted by the plurality of ultraviolet light-emitting modules 13 may sterilize the protection cover 3, avoid cross-infection of users, and improve the user experience.

To sterilize the protection cover 3 by the UV light emitted by the plurality of ultraviolet light-emitting modules 13, the protection cover 3 may be made of an ultraviolet transmittable material. In one embodiment, the material of the protection cover 3 may be transparent quartz. The UV light emitted by the ultraviolet light-emitting modules 13 may penetrate the quartz, thereby sterilizing the touch surface 31 of the protection cover 3. Further, the quartz is a transparent material, and may be able to transmit the visible light emitted from the display panel 2.

In the touch display module provided by the present disclosure, the touch panel 1 may be arranged independently of the display panel 2, or the plurality of touch electrodes 11, and the plurality of ultraviolet light-emitting modules 13 of the touch panel 1 may also be integrated on the light-exiting side the display panel 2, or the plurality of touch electrodes 11 of the touch panel 1 may also be integrated in the display panel 2, and the plurality of ultraviolet light-emitting modules 13 may be disposed on the side of the display panel 2 facing the protection cover 3. The touch electrode 11 may be a mutual capacitance touch electrode or a self-capacitance touch electrode. The substrate 10 of the touch panel 1 may be a single-layer glass substrate, or a flexible film, or a double-layer flexible film.

Figure 16:
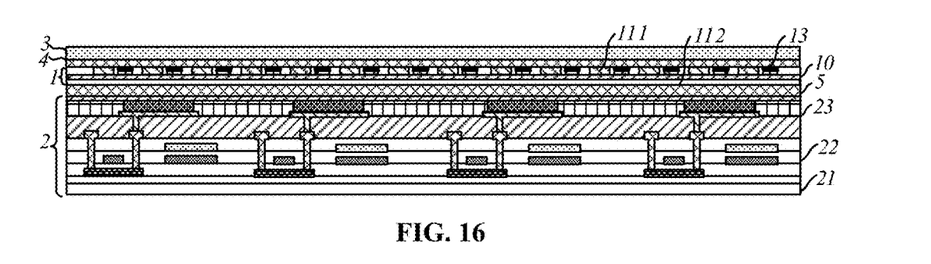
FIG. 16 illustrates another exemplary touch display module consistent with various disclosed embodiments of the present disclosure.

FIG. 16 illustrates another exemplary touch display module consistent with various disclosed embodiments of the present disclosure. As shown in FIG. 16, the touch panel 1 may be arranged independently of the display panel 2, and the touch panel 1 and the display panel 2 may be formed by bonding with each other. The touch panel 1 may be any touch panel described in FIGS. 10-13.

The display panel 2 may be an OLED display panel or an LED display panel. Taking an OLED display panel as an example, the display panel 2 may include an array substrate 21, a driving array layer 22 and a light-emitting element layer 23. The touch display module may also include a polarizing layer 4 and an encapsulating layer 5. The polarizing layer 4 may be disposed on the side of the encapsulating layer 5 facing the protection cover 3. Any of the previously described touch panel 1 may be disposed between the encapsulating layer 5 and the polarizing layer 4. Because the touch panel 1 may be integrated with the plurality of ultraviolet light-emitting modules 13, it may sterilize the protection cover 3 frequently touched by the user to prevent the cross-infection.

The driving array layer 22 may be disposed on the array substrate 21. The driving array layer 22 may include a pixel circuit, and the pixel circuit may include a plurality of thin-film transistors and capacitors.

The light-emitting element layer 23 may be disposed on the side of the driving array layer 22 away from the array substrate 21, and the light-emitting element layer 23 may include a plurality of first electrodes, light-emitting layers and a second electrode layer arranged in sequence. The light-emitting layer may include a plurality of light-emitting structures arranged as an array. The second electrode layer may be located on the side of the light-emitting layer away from the array substrate 21. Each first electrode and the region of the second electrode layer corresponding to the light-emitting structure may form a light-emitting element. Any one of the first electrode and the second electrode layer may be an anode, and the other may be a cathode. The pixel circuit may be electrically connected to each light-emitting element to drive the light-emitting element to emit light.

The encapsulation layer 5 may be located on the side of the light-emitting element layer 23 away from the array substrate 21 or on the side of the display panel 2 facing the protection cover 3. The encapsulation layer 5 may prevent water vapor from intruding from the side to affect the electrical performance of the light-emitting element layer 23.

The polarizing layer 4 may be located on the side of the encapsulation layer 5 facing the protection cover 3. The polarizing layer 4 may have a polarization direction, allowing only vibrations parallel to the polarization direction to pass through, while absorbing light that vibrates perpendicular to the polarization direction.

Figure 17:
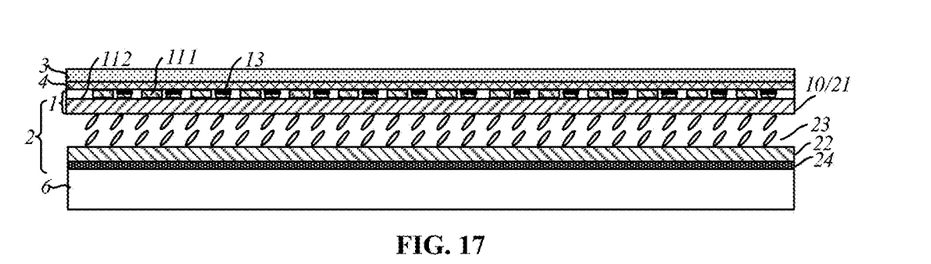
FIG. 17 illustrates another exemplary touch display module consistent with various disclosed embodiments of the present disclosure.

FIG. 17 illustrates another exemplary touch display module consistent with various disclosed embodiments of the present disclosure. As shown in FIG. 17, the touch display module may be similar in structure to the touch display module shown in FIG. 16, except that the touch electrodes 11 of the touch panel 1 may be located on the light-exiting side of the display panel 2.

The display panel 2 may be a liquid crystal display (LCD) panel 2. When the display panel 2 is an LCD panel, the touch display module may further include a backlight module 6. Since the LCD panel itself may not emit light, the backlight module 6 may provide a light source with a sufficient brightness and a uniform distribution for it to display images normally.

The display panel 2 may include a color filter substrate 21, and the touch display module may further include a polarizing layer 4. The polarizing layer 4 may be located on the side of the color filter substrate 21 facing the protection cover 3. The substrate 10 of any of the previously described touch panel 1 may be shared with the color filter substrate 21, and the plurality of touch electrodes 11 and the plurality of ultraviolet light-emitting modules 13 of the touch panel 1 may be disposed on the side of the color filter substrate 21 facing the polarizing layer 4. Because the touch panel 1 may be integrated with a plurality of ultraviolet light-emitting modules 13, it may sterilize the protection cover 3 frequently touched by the user to prevent the cross-infection.

The display panel 2 may include a color filter substrate 21, an array substrate 22, and a liquid crystal layer 23 disposed between the array substrate 22 and the color filter substrate 21. The color filter substrate 21 may be located between the array substrate 22 and the protection cover 3. The liquid crystal layer 23 may include a plurality of liquid crystal molecules. The liquid crystal molecules may be generally rod-shaped, which may flow like liquid and have certain crystal characteristics. When the liquid crystal molecules are in an electric field, their arrangement direction will change according to the change of the electric field.

The array substrate 21 may include a transparent insulating substrate (for example, glass) and a plurality of thin-film transistors, data lines, gate lines, pixel electrodes, and common electrodes, etc., formed on the insulating substrate. The color filter substrate 23 may include a transparent insulating substrate, and a color filter formed on the insulating substrate, etc.

Any one of the array substrate 22 and the color filter substrate 21 may include a common electrode. The common electrode may be made of a transparent conductive material, such as indium tin oxide (ITO), or indium zinc oxide (IZO), etc. The common electrode may be insulated from each other by the passivation layer and the pixel electrode. The liquid crystal layer 23 may be held between the color filter substrate 21 and the array substrate 22. Different voltages may be applied to the pixel electrode and the common electrode to generate an electric field to drive the liquid crystal molecules to rotate to display images.

The touch display module may also include another polarizing layer 5 located between the backlight module 6 and the array substrate 22. The polarizing layer 4 and the polarizing layer 5 may have their own polarization directions, and only allow vibrations parallel to the polarization directions to pass through, while absorbing light that vibrates perpendicular to the directions.

In such an embodiment, the substrate 10 of the touch panel 1 and the color filter substrate 21 may be shared. In another word, the plurality of touch electrodes 11 of the touch panel 1 may be mutual-capacitive touch electrodes or self-capacitance touch electrodes with a single-layer structure. The plurality of touch electrodes 11 and the plurality of ultraviolet light-emitting modules 13 may be integrated on a side of the color film substrate. 21 away from the array substrate 21. Because the touch panel 1 may reduce the substrate 10, the thickness of the touch display module may be reduced.

Figure 18:
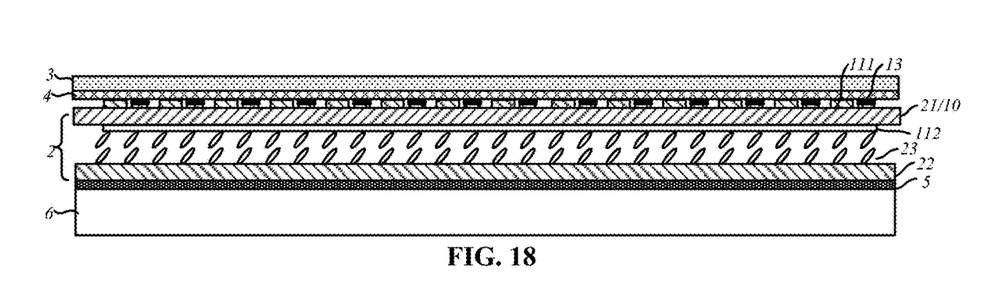
FIG. 18 illustrates another exemplary touch display module consistent with various disclosed embodiments of the present disclosure.

FIG. 18 illustrates another exemplary touch display module consistent with various disclosed embodiments of the present disclosure. As shown in FIG. 18, the touch display module may have a structure similar to the touch display module shown in FIG. 17, except that a portion of the touch electrodes 11 of the touch panel 1 may be disposed in the display panel 2.

In one embodiment, the display panel 2 may be an LCD panel. The substrate 10 of the touch panel 1 may be shared with the color filter substrate 21, at least a portion of the plurality of touch electrodes 11 may be integrated on the side of the color filter substrate 21 facing away from the protection cover 3. The plurality of ultraviolet light-emitting modules 13 may be disposed on a side of the color filter substrate 21 facing away from the protection cover 3 such that the ultraviolet light-emitting modules 13 may emit ultraviolet light toward the protection cover 3 to frequently sterilize and disinfect the protection cover 3 touched by the user to prevent the cross-infection.

As shown in FIG. 18, multiple first electrodes 111 of the plurality of touch electrodes 11 and the plurality of ultraviolet light-emitting modules 13 may be disposed on the side of the color filter substrate 21 facing the protection cover 3. Multiple second electrodes 112 of the plurality of touch electrodes 11 may be located on the side of the color filter substrate 21 away from the protection cover 3. The touch panel 1 may be a double-layer structure of mutual capacitance touch electrode. Because the substrate 10 of the touch panel 1 may be shared with the color filter substrate 21, the substrate 10 may be reduced, it may have a better light transmittance, and may be thinner and lighter, and the bezel area may be narrower.

Figure 19:
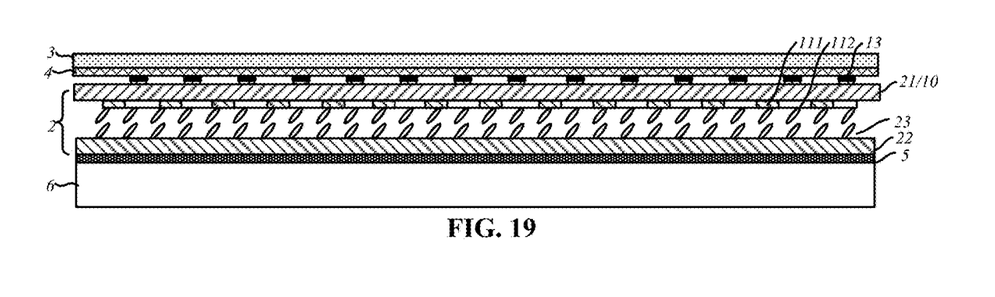
FIG. 19 illustrates another exemplary touch display module consistent with various disclosed embodiments of the present disclosure.

FIG. 19 illustrates another exemplary touch display module consistent with various disclosed embodiments of the present disclosure. As shown in FIG. 19, the touch display module may have a structure similar to the touch display module shown in FIG. 18, except that all touch electrodes 11 of the touch panel 1 may be located in the display panel 2.

For example, the first electrodes 111 and the second electrodes 112 of the touch panel 1 may be arranged on the same layer on the side of the color filter substrate 21 away from the protection cover 3. The touch panel 1 may be a mutual capacitance touch panel with a single-layer structure, or a self-capacitance touch panel with a single-layer structure.

In one embodiment, the display panel 2 may be a liquid crystal display panel. The substrate 10 of the touch panel 1 may be shared with the color filter substrate 21. The plurality of touch electrodes 11 may be integrated on the side of the color filter substrate 21 away from the protection cover 3, and the plurality of ultraviolet light-emitting modules 13 may be disposed on a side of the color filter substrate 21 facing the protection cover 3 to enable the ultraviolet light-emitting modules 13 to emit ultraviolet light toward the protection cover 3 to frequently sterilize and disinfect the protective cover 3 touched by the user to prevent the cross-infection.

As shown in FIG. 19, the plurality of ultraviolet light-emitting modules 13 may be disposed on the side of the color filter substrate 21 facing the protection cover 3, and the multiple first electrodes 111 and the multiple second electrodes 112 of the plurality of touch electrodes 11 may be disposed on the side of the color filter substrate 21 facing away from the protection cover 3. Because the substrate 10 of the touch panel 1 may be shared with the color filter substrate 21, the substrate 10 may be reduced. Thus, the touch panel 1 may have a better light transmittance, may be thinner and lighter, and the bezel area may be narrower.

Figure 20:
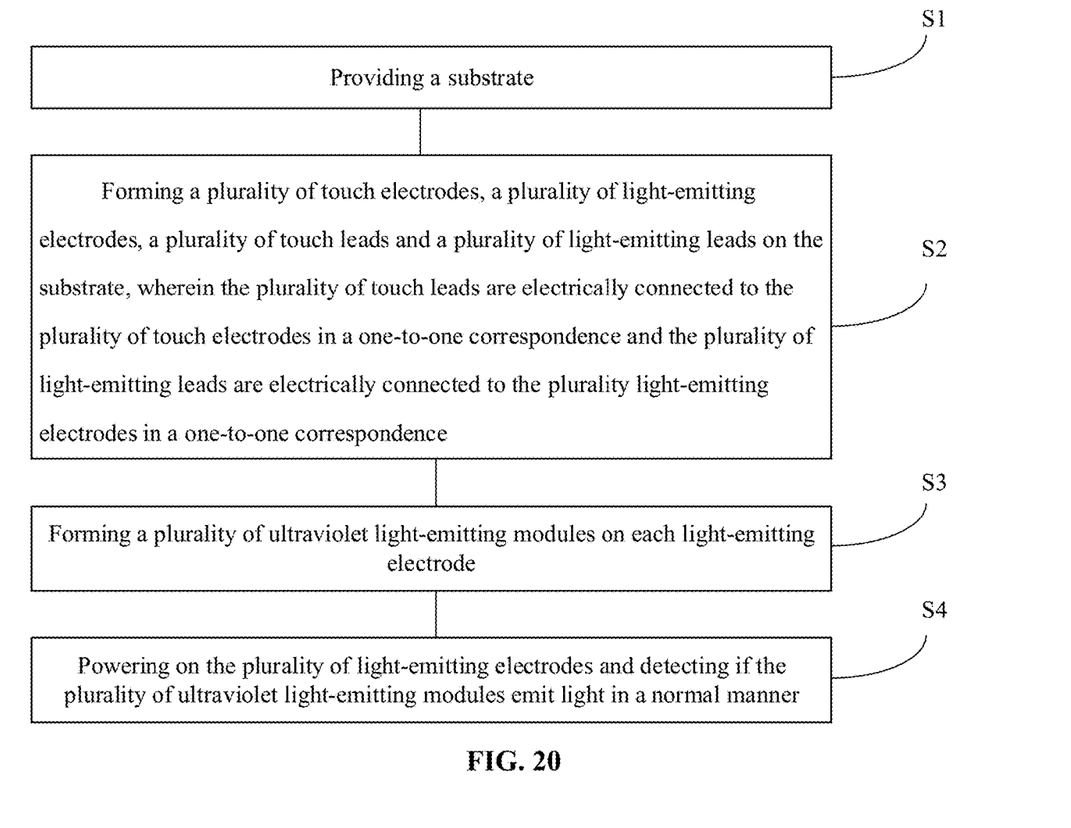
FIG. 20 illustrates a flowchart of an exemplary fabrication process of a touch panel consistent with various disclosed embodiments of the present disclosure.

The present disclosure also provides a method for forming a touch panel. FIG. 20 illustrates a flowchart of an exemplary method for forming a touch panel consistent with various disclosed embodiments of the present disclosure.

As shown in FIG. 20, the method may include: Step S1: providing a substrate 10;

Step S2: forming a plurality of touch electrodes 11, a plurality of light-emitting electrodes 131, a plurality of touch leads 12, and a plurality of light-emitting leads 14 on the substrate 10, wherein the plurality of touch leads 12 and the plurality of touch electrodes 11 may be electrically connected in a one-to-one correspondence, and the light-emitting leads 14 and the light-emitting electrodes 131 may be electrically connected in a one-to-one correspondence;

Step S3: forming a plurality of ultraviolet light-emitting elements 132 on each light-emitting electrode 131, wherein the ultraviolet light-emitting elements 132 may be bonded to the light-emitting electrodes 131 by using a surface mount technology (SMT) or a chip on board (COB) technology; and Step S4: powering on the light-emitting electrodes 131 and detecting whether the ultraviolet light-emitting elements 132 emit light in a normal manner.

In the step S2, forming the plurality of touch electrodes 11, the plurality of light-emitting electrodes 131, the plurality of touch leads 12, and the plurality of light-emitting leads 14 on the substrate 10 may include:

Step S21: forming a first pattern layer on the substrate 10, wherein the first pattern layer may include a plurality of first electrodes 111 and a plurality of first touch leads 12 extending along the first direction X;

Step S22: forming an insulating layer on the first pattern layer; and

Step S23: forming a second pattern layer on the insulating layer 10. The second pattern layer may include a plurality of second electrodes 112 and a plurality of second touch leads 12, extending along the second direction Y. The first direction X may intersect the second direction Y.

In one embodiment, when the first pattern layer or the second pattern layer is formed, a third pattern layer may also be formed. The third pattern layer may include a plurality of light-emitting electrodes 131 and a plurality of light-emitting leads 14 extending along the first direction X.

In another embodiment, a third pattern layer may also be formed on the side of the substrate 10 away from the first pattern layer and the second pattern layer. The third pattern layer may include a plurality of light-emitting electrodes 131 and a plurality of light-emitting leads 14 extending along the first direction X.

Further, the plurality of first electrodes 111, the plurality of second electrodes 112, and the plurality of light-emitting electrodes 131 may form a touch area TA on the substrate 10. The plurality of first touch leads 12, the plurality of second touch leads 12 and the plurality of light-emitting leads 14 may respectively extend from the touch area TA to the bonding area BA of the bezel area of the substrate 10, and the bonding area BA may be used for bonding flexible circuit boards or driving chips.

As shown in FIG. 10, the first pattern layer, the second pattern layer, and an insulating layer (not shown in the figure) between the first pattern layer and the second pattern layer may be formed on one side of the first surface 101 of the substrate 10. Referring to FIG. 3, the first pattern layer may include a plurality of first electrodes 111 extending along the first direction X in the touch area TA, and a plurality of first touch leads 12 extending from the plurality of first electrodes 111 to the bonding area BA. The second pattern layer may include a plurality of second electrodes 112 extending along the second direction Y in the touch area TA, and a plurality of second touch leads 12 extending from the plurality of second electrodes 112 to the bonding area BA.

Further, a third pattern layer may be formed on the side of the first surface 101 of the substrate 10. The third pattern layer may include a plurality of light-emitting electrodes 131 extending along the first direction X in the touch area TA, and a plurality of light-emitting leads 14 extending from to a plurality of light-emitting electrodes 131 to the bonding area BA.

As shown in FIG. 11, a first pattern layer, a second pattern layer, and an insulating layer (not shown in the figure) between the first pattern layer and the second pattern layer may be formed on one side of the second surface 102 of the substrate 10. Referring to FIG. 3, the first pattern layer may include a plurality of first electrodes 111 extending along the first direction X in the touch area TA, and a plurality of first touch leads 12 extending from the plurality of first electrodes 111 to the bonding area BA. The second pattern layer may include a plurality of second electrodes 112 extending along the second direction Y in the touch area TA, and a plurality of second touch leads 12 extending from the plurality of second electrodes 112 to the bonding area BA.

Further, a third pattern layer may be formed on the side of the first surface 101 of the substrate 10. The third pattern layer may include a plurality of light-emitting electrodes 131 extending along the first direction X in the touch area TA, and a plurality of light-emitting leads 14 extending from the plurality of light-emitting electrodes 131 to the bonding area BA.

When the first pattern layer and the second pattern layer are located on different sides of the substrate 10, any one of the first pattern layer and the second pattern layer may further include a plurality of light-emitting electrodes 131 located in the touch area TA and in parallel with the plurality of first electrodes 111 or the plurality of second electrodes 112, and a plurality of light-emitting leads 14 extending from the plurality of light-emitting electrodes 131 to the bonding area BA.

As shown in FIG. 12, a first pattern layer and a third pattern layer may be formed a side of the first surface 101 of the substrate 10, and a second pattern layer may be formed on a side of the second surface 102 of the substrate 10. Referring to FIG. 3, the first pattern layer may include a plurality of first electrodes 111 in the touch area A and extending along the first direction X, and a plurality of first touch leads 12 extending from the plurality of first electrodes 111 to the bonding area BA. The second pattern layer may include a plurality of second electrodes 112 extending along the second direction Y and in the touch area TA, and a plurality of second touch leads 12 extending from the plurality of second electrodes 112 to the bonding area BA. The third pattern layer may include a plurality of light-emitting electrodes 131 extending along the first direction X and in the touch area TA, and a plurality of light-emitting leads 14 extending from the plurality of light-emitting electrodes 131 to the bonding area BA.

As shown in FIG. 13, a first pattern layer and a third pattern layer may be formed on a side of the first flexible substrate 10a of the substrate 10, and a second pattern layer may be formed on a side of the second flexible substrate 10b of the substrate 10. An insulating layer may be formed between the first flexible substrate 10a and the second flexible substrate 10b. Referring to FIG. 3, the first pattern layer may include a plurality of first electrodes 111 extending along the first direction X and in the touch area TA, and a plurality of first touch leads 12 extending from the plurality of first electrodes 111 to the bonding area BA. The second pattern layer may include a plurality of second electrodes 112 extending along the second direction Y and in the touch area TA, and a plurality of second touch leads 12 extending from the plurality of second electrodes 112 to the bonding area BA. The third pattern layer may include a plurality of light-emitting electrodes 131 extending along the first direction X and in the touch area TA, and a plurality of light-emitting leads 14 extending from the plurality of light-emitting electrodes 131 to the bonding area BA.

The touch display module provided by the present disclosure may include a touch panel 1, a display panel 2, and a protection cover 3. The substrate 10 of the touch panel 1 may be a glass substrate or a flexible film substrate, and the substrate 10 may be independent of the display panel 2. The substrate 10 may also be shared with the encapsulation layer or the color filter substrate of the display panel 1. By integrating a plurality of ultraviolet light-emitting modules 13 and a plurality of touch electrodes 11 on the substrate 10, and the plurality of ultraviolet light-emitting modules 13 may be located on the side of the substrate 10 facing the protection cover 3 such that the ultraviolet light-emitting modules 13 may emit the ultraviolet light toward the protection cover 3 to frequently sterilize and disinfect the touch surface 31 of the protection cover 3 touched by the users to avoid the cross-infection of the users and improve the user experience.

Thus, in the present disclosure, the substrate of the touch panel may include a touch area and a bonding area located on one side of the touch area. A plurality of touch electrodes and a plurality of ultraviolet light-emitting modules may be disposed in the touch area, and the touch lead electrically connected to each touch electrode and the light-emitting lead electrically connected to each ultraviolet light-emitting module may extend to the bonding area. Thus, the touch surface of the touch display module may be automatically sterilized to avoid the cross-infection of users, and the user experience may be improved.

Although the present disclosure has been described with reference to the preferred embodiments, without departing from the scope of the present disclosure, various modifications can be made thereto, and the components therein can be replaced with equivalents. In particular, as long as there is no structural conflict, the various technical features mentioned in the various embodiments can be combined in any manner. The present disclosure may not be limited to the specific embodiments disclosed in the text, but includes all technical solutions falling within the scope of the claims.

What is claimed is:

1. A touch panel, comprising:
   a substrate, including a touch area and a bonding area located at one side of the touch area;
   a plurality of touch electrodes, located in the touch area;
   a plurality of touch leads, connected with the plurality of touch electrodes in a one-to-one correspondence and extending to the bonding area;
   a plurality of ultraviolet light-emitting modules, located in the touch area; and
   a plurality of light-emitting leads, electrically connected with the plurality of ultraviolet light-emitting modules in a one-to-one correspondence and extending to the bonding area.

2. The touch panel according to claim 1, wherein:
   the plurality of ultraviolet light-emitting modules are distributed in parallel along a first direction;
   each of the plurality of ultraviolet light-emitting modules includes a plurality of light-emitting electrodes extending along a second direction and a plurality of ultraviolet light-emitting elements electrically connected to the plurality of light-emitting electrodes;
   the plurality of ultraviolet light-emitting elements are distributed and spaced apart along a second direction; and
   the first direction intersects the second direction.

3. The touch panel according to claim 2, wherein:
   each ultraviolet light-emitting module includes a first terminal and a second terminal;
   each light-emitting electrode includes a plurality of sub light-emitting electrodes spaced apart along the second direction;
   each sub light-emitting electrode includes a first end and a second end disposed opposite to the first end;
   the second end of one of every two adjacent sub light-emitting electrodes is electrically connected to the first terminal of the ultraviolet light-emitting module; and
   the first end of another of the every two adjacent sub light-emitting electrodes is electrically connected to the second terminal of the ultraviolet light-emitting module.

4. The touch panel according to claim 3, wherein the plurality of light-emitting leads comprise:
   a plurality of first light-emitting leads, wherein each of the plurality of first light-emitting leads is electrically connected to sub light-emitting electrodes at one end along the second direction of the plurality of sub light-emitting electrodes of each ultraviolet light-emitting module;
   a plurality of second light-emitting leads, wherein each of the plurality of second light-emitting leads is electrically connected to sub light-emitting electrodes at another end along the second direction of the plurality of sub light-emitting electrodes of each ultraviolet light-emitting module; and
   a third light-emitting lead, electrically connected with the plurality of first light-emitting leads,
   wherein the third light-emitting lead and the plurality of second light-emitting leads respectively extend to the bonding area.

5. The touch panel according to claim 2, wherein:
   the ultraviolet light-emitting element includes a first terminal and a second terminal;
   the ultraviolet light-emitting module includes two light-emitting electrodes disposed side-by-side;
   the first terminal of the ultraviolet light-emitting element is electrically connected to one of the two light-emitting electrodes; and
   the second terminal of the ultraviolet light-emitting element is electrically connected to another of the two light-emitting electrodes.

6. The touch panel according to claim 5, wherein the plurality of light-emitting leads comprise:
   a plurality of first light-emitting leads, wherein each first light-emitting lead is electrically connected to one of the two light-emitting electrodes of each ultraviolet light-emitting module;
   a plurality of second light-emitting leads, wherein each second light-emitting lead is electrically connected to another of the two light-emitting electrodes of the each ultraviolet light-emitting module; and
   a third light-emitting lead, electrically connected with the plurality of first light-emitting leads,
   wherein the third light-emitting lead and the plurality second light-emitting leads respectively extend to the bonding area.

7. The touch panel according to claim 2, wherein:
   the plurality of touch electrodes include a plurality of first electrodes and a plurality of second electrodes insulated from each other;
   one of the plurality of first electrodes and the plurality of second electrodes extend along the first direction and are in parallel with the light-emitting electrode; and
   another of the plurality of first electrodes and the plurality of second electrodes extend along the first direction.

8. The touch panel according to claim 7, wherein:
   the substrate includes a first surface and a second surface disposed opposite to the first surface; and
   the plurality of ultraviolet light-emitting modules and any one of the plurality of first electrodes and the plurality of second electrodes are disposed on the first surface and another of the plurality of first electrodes and the plurality of second electrodes are disposed on the second surface; or
   the plurality of ultraviolet light-emitting modules are disposed on the first surface and the plurality of first electrodes and the plurality of second electrodes are disposed on the second surface.

9. The touch panel according to claim 7, wherein:
   the substrate includes a first flexible substrate and a second flexible substrate insulated to each other;
   the plurality of ultraviolet light-emitting modules and any one of the plurality of first electrodes and the plurality of second electrodes are disposed on the first flexible substrate; and
   another of the plurality of first electrodes and the plurality of second electrodes are disposed on a side of the second flexible substrate facing the first flexible substrate.

10. The touch panel according to claim 1, wherein:
    the substrate includes a first surface and a second surface disposed opposite to the first surface;

the plurality of touch electrodes are disposed on the first surface; and the plurality of ultraviolet light-emitting modules are disposed on a side of the plurality of touch electrodes away from the substrate.

11. A touch module, comprising:

a protection cover, having a touch surface; and a touch panel according to claim 1, disposed on a side of the protection cover away from the touch surface, wherein the plurality of ultraviolet light-emitting modules of the touch panel are disposed on a side of the substrate facing the protection cover.

12. A touch display module, comprising:

a protection cover, including a touch surface;

a display panel, disposed on a side of the protection cover away from the touch surface; and a touch panel, disposed between the touch panel and the protection cover and including:

a substrate, including a touch area and a bonding area located at one side of the touch area;

a plurality of touch electrodes, located in the touch area;

a plurality of touch leads, connected with the plurality of touch electrodes in a one-to-one correspondence and extending to the bonding area;

a plurality of ultraviolet light-emitting modules, located in the touch area; and a plurality of light-emitting leads, electrically connected with the plurality of ultraviolet light-emitting modules in a one-to-one correspondence and extending to the bonding area, wherein the plurality of ultraviolet light-emitting modules are disposed on a side of the substrate facing the protection cover.

13. The touch display module according to claim 12, wherein:

the display panel is a light-emitting diode display panel;

the touch display module also includes a polarizing layer and an encapsulation layer;

the encapsulation layer is disposed on a side of the display panel facing the protection cover;

the polarizing layer is disposed on a side of the encapsulation layer facing the protection cover; and the touch panel is disposed between the encapsulation layer and the polarizing layer.

14. The touch display module according to claim 12, wherein:

the display panel is a liquid crystal display panel;

the display panel includes a color filter substrate;

the touch display module also includes a polarizing layer;

the polarizing layer is disposed on a side of the color filter substrate facing the protection cover;

the substrate of the touch panel is shared with the color filter substrate; and the plurality of touch electrodes and the plurality of ultraviolet light-emitting modules of the touch panel are disposed on a side of the color filter substrate facing the polarizing layer.

15. The touch display module according to claim 12, wherein:

the display panel is a liquid crystal display panel;

the touch display module includes a color filter substrate;

the substrate of the touch panel is shared with the color filter substrate;

at least a portion of the plurality of touch electrodes are disposed on a side of the color filter substrate away from the protection cover; and the plurality of ultraviolet light-emitting modules are disposed on a side of the color filter substrate facing the protection cover.

16. The touch display module according to claim 12, wherein:

the protection cover is made of a ultraviolet transmittable material.

17. The touch display module according to claim 12, wherein:

the protection cover is made of a material including quartz.

18. The touch display module according to claim 12, wherein:

the touch display panel also includes a main circuit board and a control chip disposed on the main circuit board;

the touch display module also includes a flexible circuit board; and one end of the flexible circuit board is bonded to the bonding area of the touch panel; and another end of the flexible circuit board is bonded with the main circuit board to allow the control chip to control on/off of the plurality of ultraviolet light-emitting modules.

19. The touch display module according to claim 18, wherein:

the control circuit includes a delay module, configured to receive first information for turning on the sterilization and disinfection mode and, according to the first information transmit second information to the plurality of ultraviolet light-emitting modules for turning on the plurality of ultraviolet light-emitting modules after delaying a preset time length.

20. A method for forming a touch panel, comprising:

providing a substrate;

forming a plurality of touch electrodes, a plurality of light-emitting electrodes, a plurality of touch leads and a plurality of light-emitting leads on the substrate, wherein the plurality of touch leads are electrically connected to the plurality of touch electrodes in a one-to-one correspondence and the plurality of light-emitting leads are electrically connected to the plurality light-emitting electrodes in a one-to-one correspondence;

forming a plurality of ultraviolet light-emitting elements on each light-emitting electrode; and powering on the plurality of light-emitting electrodes and detecting if the plurality of ultraviolet light-emitting modules emit light in a normal manner.

\* \* \* \* \*